United States Patent
Park et al.

(10) Patent No.: US 7,509,237 B2
(45) Date of Patent: Mar. 24, 2009

(54) TEST SYSTEM AND TEST METHOD USING VIRTUAL REVIEW

(75) Inventors: Ho Sun Park, Paju-si (KR); Moon Seong Eom, Paju-si (KR); Sang Ho Nam, Paju-si (KR)

(73) Assignee: LG. Display Co., Ltd., Seoul (KR)

( * ) Notice: Subject to any disclaimer, the term of this patent is extended or adjusted under 35 U.S.C. 154(b) by 41 days.

(21) Appl. No.: 11/644,637

(22) Filed: Dec. 22, 2006

(65) Prior Publication Data
US 2007/0159179 A1 Jul. 12, 2007

(30) Foreign Application Priority Data
Dec. 30, 2005 (KR) .................. 10-2005-0135812
Nov. 21, 2006 (KR) .................. 10-2006-0114947

(51) Int. Cl.
*G06F 11/22* (2006.01)
*G06F 17/00* (2006.01)

(52) U.S. Cl. ............... 702/185; 702/117; 702/118; 382/149

(58) Field of Classification Search ............. 702/185, 702/117, 118, 187–189
See application file for complete search history.

(56) References Cited

U.S. PATENT DOCUMENTS

| | | | |
|---|---|---|---|
| 6,480,279 B2 * | 11/2002 | Nara et al. | 356/394 |
| 6,721,045 B1 * | 4/2004 | Hunter | 356/237.5 |
| 7,269,280 B2 * | 9/2007 | Hiroi et al. | 382/149 |
| 2002/0161532 A1 * | 10/2002 | Dor et al. | 702/35 |
| 2003/0193347 A1 * | 10/2003 | Ito et al. | 324/770 |
| 2006/0065645 A1 * | 3/2006 | Nakasu et al. | 219/121.68 |
| 2007/0294058 A1 * | 12/2007 | KITAMOTO et al. | 702/188 |

* cited by examiner

Primary Examiner—Hal D Wachsman
(74) Attorney, Agent, or Firm—Brinks Hofer Gilson & Lione (57) ABSTRACT

Disclosed are a test system and a test method using a virtual review based on a captured image of a defect on a substrate. The test system using a virtual review comprises: a test device that takes an image of a defect on an array substrate or color filter substrate to acquire a captured image and provides an information an related to the defect. A main server stores the captured image and the information related to the defect from the test device at a database and transmits them to a review host. The review host determines whether a defect exists on the array substrate or color filter substrate based on the information related to the defect from the main server to yield a determination result and resends the determination result to the main server.

21 Claims, 7 Drawing Sheets

TEST SYSTEM AND TEST METHOD USING VIRTUAL REVIEW

This nonprovisional application claims priority under 35 U.S.C. § 119(a) to patent application Ser. No. 10-2005-0135812 filed in Republic of Korea on Dec. 30, 2005, and patent application Ser. No. 2006-0114947 filed in Republic of Korea on Nov. 21, 2006, the entire contents of which are hereby incorporated by reference.

BACKGROUND Of THE INVENTION

1. Field of the invention

The present invention relates to a test system and a test method using a virtual review, and more specifically, to a test system and a test method using a virtual review for testing whether there is a defect on a thin film transistor substrate or a color filter substrate.

2. Related Art

With the recent increase of interest in information display devices, flat panel displays (FPDs) have been studied and commercialized as a means to replace existing display devices such as CRTs. Among these flat panel displays, a liquid crystal display (LCD), which requires optical anisotropy of the liquid crystal to display an image, has been widely used as a monitor for laptop computers, desktop computers, etc. because of its good resolution, capability of displaying an image, and image quality.

A liquid crystal display typically comprises an array substrate, a color filter substrate, and a liquid crystal layer between the array substrate and the color filter substrate.

The array substrate comprises: gate lines and data lines, both arranged on the array substrate in horizontal and vertical directions to define pixel regions; switching elements such as thin film transistors arranged on the intersection regions of the gate lines and data lines; and pixel electrodes formed on the pixel regions.

The color filter substrate comprises: a color filter comprising sub-filters R, G, B to implement colors; and a black matrix to separate between the sub-filters to thereby define pixel regions and to block light transmitting the liquid crystal layer. The color filter substrate can further comprise transparent common electrodes, which are arranged on the array substrate, to apply voltages to the liquid crystal layer.

The array substrate and color filter substrate configured as above are attached to each other by a sealant to thereby complete a liquid crystal panel.

The liquid crystal display can generally be manufactured through an array process, a color filter process, a cell process, and a module process.

The array process is a process that forms arrays of thin film transistors on a first substrate, which is a transparent insulating substrate, by repeating deposition, photolithography, and etching. The color filter process is a process that forms a black matrix to block light from passing through regions other than pixel regions and to make red, green, and blue color filters (R, G, B) using dyes or pigments.

Before the cell process, an additional process is required to evaluate the state of the manufactured array substrate and color filter substrate. The array and the color filter are tested to determine whether there is a defect on the array substrate and color filter substrate, to eliminate substrates having defects from the cell process.

The cell process is a process used to form liquid crystal panel cells. In this process the first substrate, which has been completed through the thin film transistor process, is attached to the second substrate, which has been completed through the color filter substrate. The substrates are attached such that they have a constant gap therebetween and then liquid crystal is injected or dropped therebetween. The module process is a process used to form modules by providing a circuit unit for signal processing, connecting the liquid crystal panel and circuit unit through a well-known mounting scheme, and then attaching them to a feature.

The above cell process will be described below in more detail.

First, alignment films are disposed on each of the array substrate, formed through the array process, and the color filter substrate, formed through the color filter process. Then a rubbing process is used to provide an anchoring force or surface adhesive force to liquid crystal molecules of the liquid crystal layer, which is provided between the array substrate and color filter substrate. At this time, the alignment films can undergo washing before applying, alignment film printing, and alignment film testing, and rubbing in the above-stated order.

Subsequently, the array substrate and color filter substrate each are washed out, a spacer is provided to keep cell gaps constantly on the array substrate, and a sealing material is applied to the circumference of the color filter. Then, the array substrate and color filter substrate are pressured to be attached to each other.

Finally, liquid crystal is injected into each liquid crystal panel through liquid crystal inlets and the inlets are sealed to form a liquid crystal layer.

Before the cell process is performed, the array substrate and color filter substrate are tested to determine whether there are any defects. More specifically, the array substrate and color filter are examined to determine whether there is any fault on their appearances and electrical wirings. For example, the process is performed to determine the appearance of color filter protrusions, oblique line stains, rubbing strips, pin holes, short circuits or disconnections in the gate lines and data lines and the like.

A test system for performing the testing process comprises a group of test devices for testing whether there is a defect on the array substrate and color filter substrate and a repair system for repairing the substrates if a fault occurs on the substrates.

The group of test devices comprises a test device for testing whether the array substrate and color filter substrate have any defect or not, a system computer for driving the test device, and a monitor connected to the system computer. Here, a keyboard and a mouse are added to the system computer to operate the system computer. In addition, a review monitor is added to the group of test devices, through which an operator can see whether there is a defect on the substrates.

In a prior art test system, one review monitor was connected to only one computer for repair in a one-to-one manner, so that one inspector could control only one test device. Therefore, there existed a problem in that work efficiency was decreased due to time loss, for example, because the test device doesn't operate during the inspector's meal times or break times. Furthermore, the prior test system had a problem in that it required inspectors as many as the number of test devices.

SUMMARY

A test system is disclosed that comprises: a test device for taking an image of a defect on an array substrate or color filter substrate to acquire a captured image and providing examination information related to the defect. A main server is used to construct the examination information from the test device as a database and then transmit them to a review host. A review host determines whether there is a defect on the array substrate or color filter substrate based on the examination information from the main server to yield a determination result. The determination result is resent to the main server.

In preferred embodiments, the examination information related to the defect may comprise an ID of the array substrate or color filter substrate, IDs of a plurality of panels provided on the array substrate or color filter substrate, number of the defect according to detected order, an image file capturing the defect, and number of the test device having detected the defect.

The determination result may comprise a case where the defect is required to be repaired, a case where the state of defect is good, a case where the state of defect is not good, and a case where the state of defect is difficult to determine.

A test method is also disclosed that comprises: taking an image of a defect on an array substrate or color filter substrate to acquire a captured image and providing examination information related to the defect from a test device; constructing the examination information from the test device as a database by a main server and then transmitting them; and determining whether there is a defect on the array substrate or color filter substrate based on the examination information from the main server to yield a determination result and resending the determination result to the main server.

DETAILED DESCRIPTION OF EMBODIMENTS

Further detailed description of the other embodiments will be contained in the accompanying detailed description and drawings. The above and/or other aspects and advantages of the prevent invention will become apparent and more readily appreciated from the following description of the exemplary embodiments, taken in conjunction with the accompany drawings. Like reference numerals refer to like elements throughout.

Hereinafter, a test system and a test method using a virtual review will be detailed with reference to accompanying drawings.

Figure 1:
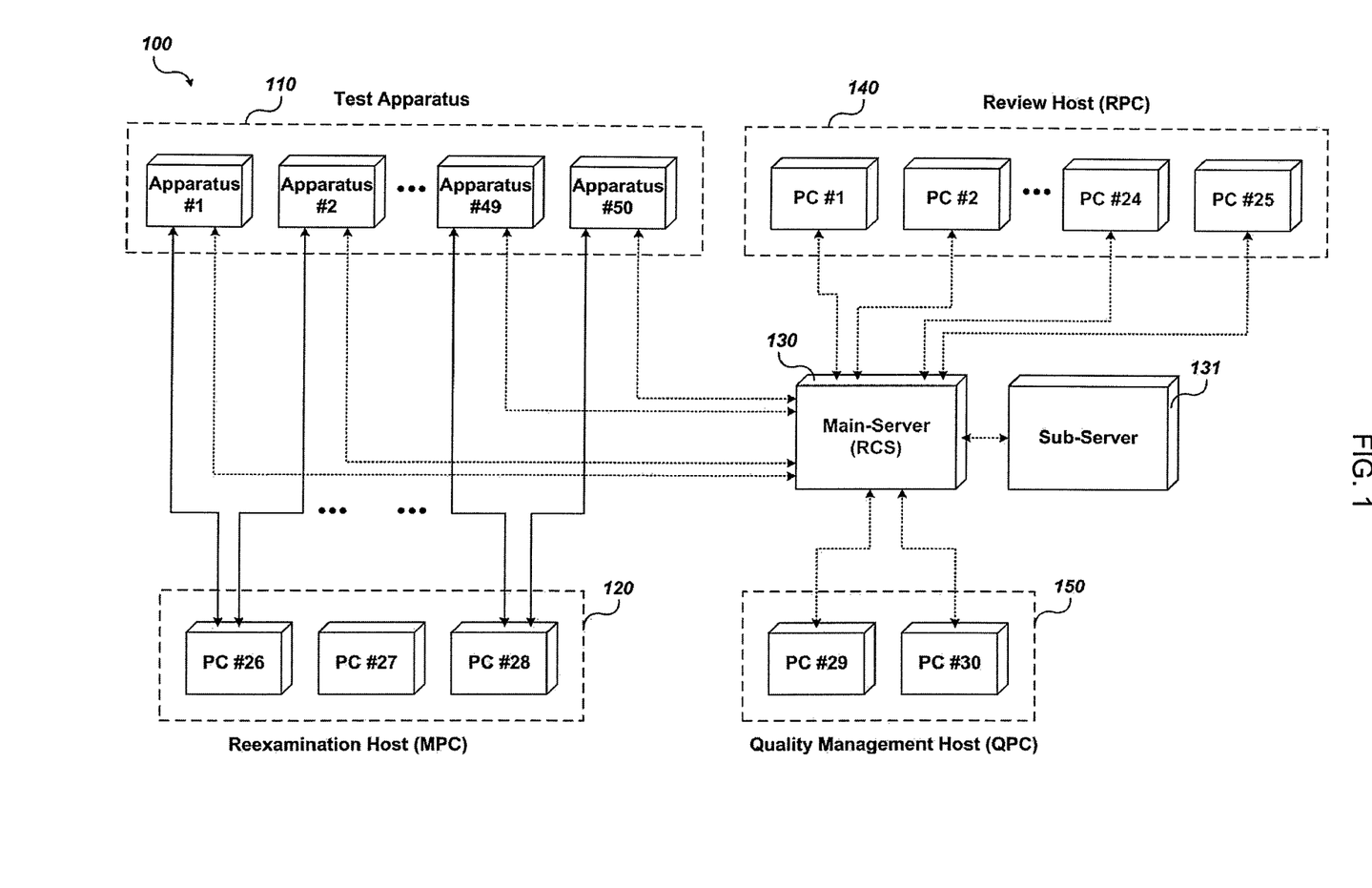
FIG. 1 is a view of illustrating a construction of a test system using a virtual review according to a first embodiment of the present invention.

FIG. 1 is a view of illustrating a construction of a test system using a virtual review according to a first embodiment of the present invention. In FIG. 1, signal flows shown as dotted lines represent having transmitted information, and signal flows shown as solid lines represent signals of actually driving test devices.

Referring to FIG. 1, a test system 100 according to an embodiment of the present invention comprises a test device 110, a reexamination host (MPC: 120), a main server (RCS: 130), a review host (RPC: 140), and a quality management host (QPC: 150). The test device 110, review host 140, and quality management host 150 each are connected to the main server 130 over a network, and the reexamination host 120 and test device 110 can be connected to each other over a separate network. The hosts 120, 140, 150 can be implemented using personal computers, i.e. PCs.

Generally, the test device 110 comprises a vision unit mounted with a camera for detecting patterns shown on a panel and a computer system for analyzing signals inputted to the camera.

The camera performs scanning on the panel in a horizontal direction to collect a pattern for test appearing on the array substrate or color filter substrate and to transfer the pattern to the computer system. The ability of detecting a defect is improved by performing the scanning, with the camera declined by a prescribed angle (e.g. 0°~70°, 80°~100°, 110°~160°), so that a defect detected differently according to viewing angle is complemented.

As such, the limitation to test through an operator's eyes can be complemented by providing a vision device such as a camera to the test device, and thus work efficiency can be improved, which can in turn raise the productivity.

On the other hand, the test device 110 performs auto defect repair (ADR) against a defect according to a first embodiment.

The main server 130 receives an image file of defect captured by the test device 110, a panel ID of the array substrate and color filter substrate, an ID of a glass substrate, numbers of the defect, number of the device, etc. and makes them a database, and then sends this information to the review host 140. An auxiliary server, i.e. a sub-server 131 can be provided in addition to the main server 130 to operate for unexpected emergencies. That is, the sub-server 131 can supplant the main server 130 in case of breakdown of the main server 130.

The review host 140 serves to review the state of defect using the captured image of defect, and determines the state of defect to thereby yield a determination value. The yielded determination value is transmitted to the main server 130 and stored at a database. The database may be implemented within the main server 130 or outside and independent of the main server 130.

After the test device 110 completes the auto repair of the defect, the quality management host 150 determines whether the defect was successfully repaired based on information of image capturing repaired region. If the defect was repaired successfully, then a subsequent array substrate or color filter substrate undergoes the test for determining whether it has any defect or not.

The reexamination host 120 serves to reexamine the state of defect in the case where the review host 140 has determined that it is difficult to determine the state of defect. While the review host 140 performs a review and a determination based on captured image of defect, the reexamination host 120 carries them out based on real-time an image taken by the camera of the test device 110 in real time.

Assuming, for example, that the number of test devices 110 is 50, 50 PCs for inspection were required for test in the prior art, but 25 review hosts 140 can be enough to perform the test because the test can be carried out not by a real time image but by a captured image in the embodiment of the present invention. And, each host 120, 140, 150 is installed at remote sites to control the test device 110 from the remote sites.

Figure 2:
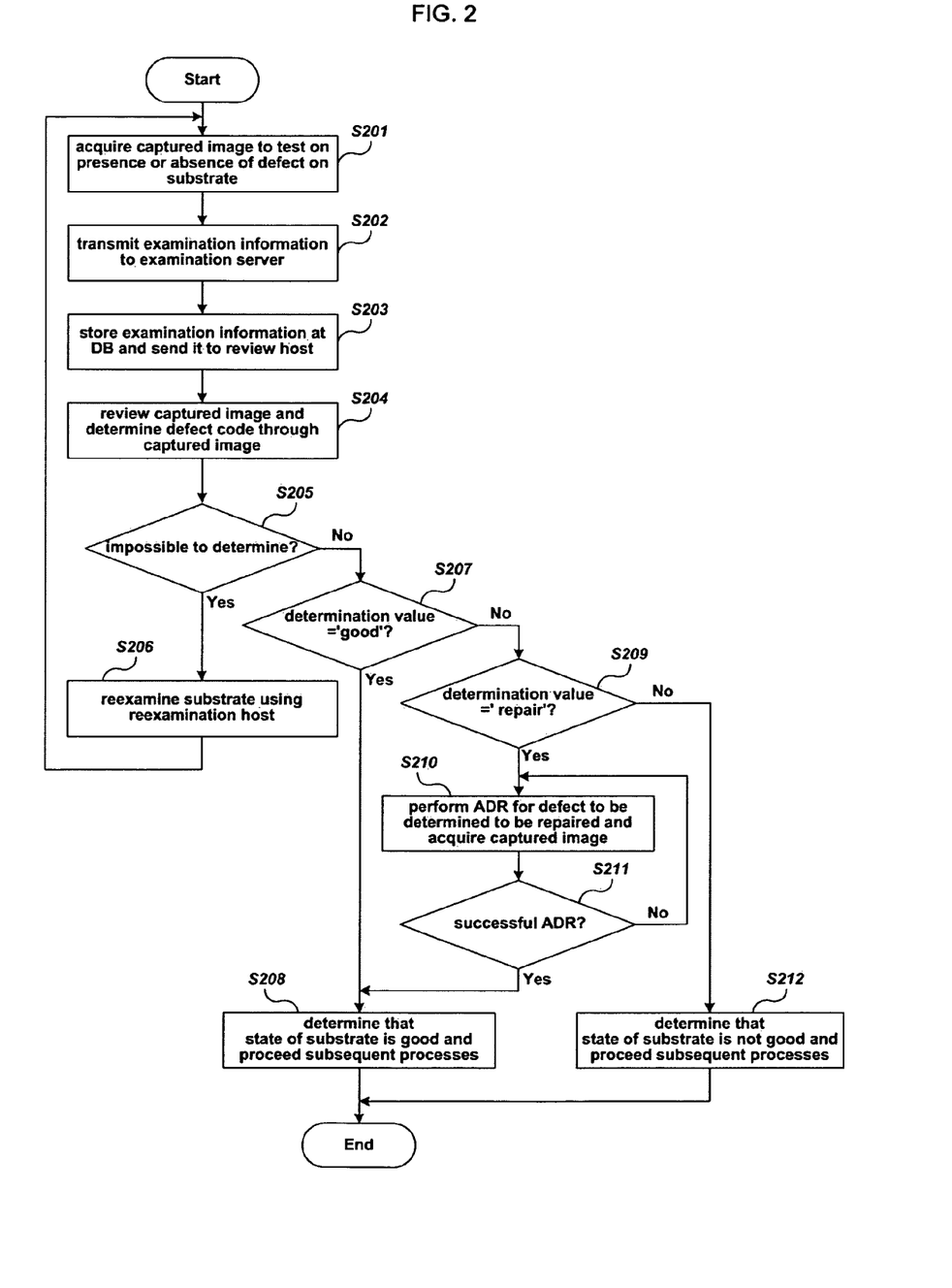
FIG. 2 is a flow chart of illustrating an operation of a test method using a virtual review according to the first embodiment of the present invention.

FIG. 2 is a flow chart of illustrating an operation of a test method using a virtual review according to the first embodiment of the present invention.

Referring to FIG. 2, first, if a glass substrate is loaded, the test device 110 determines whether a defect on the array substrate or color filter substrate exists. If any defect is detected on the array substrate or color filter substrate, then the test device captures an image of the detected defect (S201).

Then, the test device 110 sends defect information, for example, information including a glass substrate identification GLS ID, a panel identification PNL ID, a defect serial number, etc. and information including a defect image file and the device number for each of the detected defect to the main server 130 (S202). Here, the GLS ID, which is information of a glass substrate for the array substrate or color filter substrate, refers to an ID of the glass substrate, e.g. such as "7AA5D017510", the PNL ID, which is information provided on the glass substrate, refer to an ID for the panel, e.g. such as "7AA5D017510A1", and the defect serial number refers to a number assigned sequentially to each defect in the case where a plurality of defects exist on one glass substrate.

The main server 130 stores the defect information and the information such as an image file, a device number, etc. transmitted from the test device 110 at the database, and then sends them to the review host 140 sequentially (S203).

If the defect information and the information such as an image file, a device number, etc. are transmitted from the main server 130 to the review host 140, then the review host 140 performs a review and a determination based on the captured image of defect (S204). That is, an operator opens the captured image file of defect to review the defect and determine the state of the defect.

At this time, various determination values can be acquired as a result of the determination by the operator, and these determination values are transmitted to the main server 130. The below table 1 shows these determination values.

TABLE 1

| Determination value | description |
| --- | --- |
| G | Good |
| N | Not good |
| P | Repaired |
| Q | impossible to determine |
| A | impossible to determine |
| M | impossible to determine |

Referring to Table 1, the determination value "Q" means the magnification adjustment of the camera is required for the review and determination because it is difficult to determine the state of defect by the captured image file. The determination values "A" means it is difficult to determine the state of defect only by the captured image file since the auto focus of the camera doesn't work appropriately. The determination value "M" means it is impossible to determine the state of defect by the review host 140 due to poor metallicity. The determination value "G" means the state of defect is good since the array substrate or color filter substrate has no defect thereon or, if any, too little defect to be considered to be crucial, and the determination value "P" means the defect of the panel are needed to repair.

In other words, it is determined in the step S205 whether the defect on the array substrate or color filter substrate is possible to evaluate or not. At this time, the determination values "Q", "A", and "M" which mean it is difficult to determine the state of defect represent the cases where the review host 140 has an difficulty in determining the state of defect.

In the case where any one of "Q", "A", and "M" is yielded as a determination value, the reexamination host 120 performs a reexamination on the defect (S206). While the review host 140 performs a review and a determination based on captured image of defect, the reexamination host 120 carries out the review and determination based on real-time an image of the array substrate or color filter substrate taken by the camera of the test device 110 in real time.

That is, an operator performs the reexamination on the defect using PCs within the reexamination host 120 which can multi-access each test device 110. At this time, a multi-access ratio of the reexamination host 120 and test device 110 may be approximately 3 to 8.

On the other hand, in the case where it is possible to determine whether there is a defect on the array substrate and color filter substrate, it is determined in the step S207 whether the determination value is "G" which means 'good', and if the determination value is "G", then the array substrate and color filter substrate are determined to be good and subsequent processes are carried out (S208).

Unless the determination value is determined to be 'good', it is determined whether the determination value is "P" which means to be repaired (S209).

If the determination value is "P", the main server 130 sends information related to the defect, and sends information that the determination value is "P", to the test device 110 at which corresponding defect is detected. If the test device 110 receives the information that the determination value is "P" from the main server 130, the test device 110 repairs the corresponding defect automatically and captures an image of the repaired region (S210). At this time, the captured image of repaired region is transmitted to the main server 130.

Subsequently, the main server 130 stores the captured image of repaired region transmitted from the test device 110 at the database and then resends them to the quality management host 150.

Next, the quality management host 150 determines whether the defect was repaired successfully, i.e. whether ADR (Auto defect repair) was successful or not, using the captured image of repaired region transmitted from the server 130 (S211).

Then, if the result of ADR showed that the defect was successfully repaired, more specifically, the defect was successfully repaired and it was determined that a defect did not exist on the array substrate or color filter substrate, the above mentioned step S208 continues and subsequently the next array substrate or color filter substrate may undergo the test to determine whether a defect exists or not.

In the case where the defect still exists in spite of the defect having been repaired, i.e., the ADR is not determined to be successful, then the test device 110 returns this process to the step S210 of repairing defect.

If the determination value is not "P", which means to be repaired, then the array substrate or color filter substrate is determined to have a defect and subsequent processes are performed (S212).

Here, the step S205, step S207, and step S209 can be changed in their order.

Figure 3:
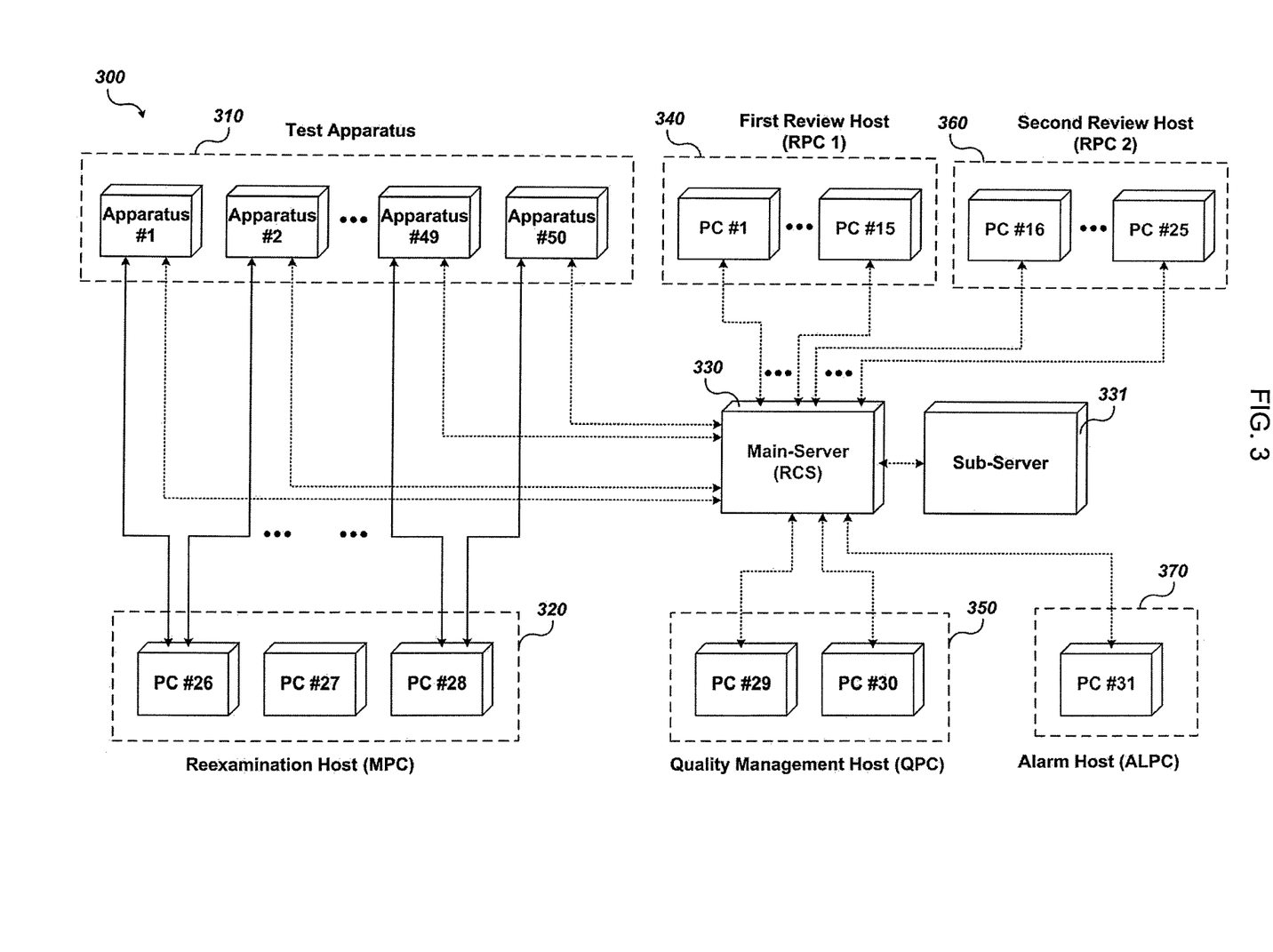
FIG. 3 is a view of illustrating another construction of a test system using a virtual review according to a second embodiment of the present invention.

FIG. 3 is a view of illustrating another construction of a test system using a virtual review according to a second embodiment of the present invention.

Referring to FIG. 3, a test system 300 using a virtual review according to the second embodiment of the present invention comprises a test device 310, a reexamination host (MPC:

320), a main server (RCS: 330), a first review host (RPC: 340), a quality management host (QPC: 350), a second review host 360, and an alarm host (ALPC: 370).

The test device 310, the first and second review hosts 340 and 360, and quality management host 350 each are connected to the main server 330 over a network, and the reexamination host 320 and test device 310 can be connected to each other over a separate network. The hosts 320, 340, 350, 360, and 370 can be implemented using personal computers, i.e. PCs.

The test system 300 using a virtual review according to the second embodiment of the present invention has the same components as the test system 100 using a virtual review according to the first embodiment of the present system except that the test system 300 further comprises the second review host 360 and alarm host 370. Therefore, the same descriptions as the test system 100 will be omitted and only differences from the test system 100 will be described hereinafter.

The test device 310 performs auto defect repair (ADR) on defects according to the second embodiment of the present invention.

The main server 330 receives an image file of defect captured by the test device 310, a panel ID, an ID of a glass substrate, numbers of the defect, number of the device, etc. and constructs a database, and then sends this information to the review host 340.

An auxiliary server, i.e. a sub-server 330 can be provided to operate for unexpected emergencies besides the main server 331. The first review host 340 serves to review the state of defect using the captured image of defect, and determines the state of defect to thereby yield a determined value. The yielded determination value is transmitted to the main server 330 and stored at a database.

After the test device 310 completes the auto repair of the defect, the second review host 360 determines whether the defect was successfully repaired based on information of an image capturing repaired region. As can be seen from the above description, the functions performed by the quality management host 150 in the first embodiment can be carried out by the second review host 360 in the second embodiment.

The reexamination host 320 serves to reexamine the state of defect in the case where the first review host 340 has determined that it is difficult to determine the state of defect. While the first review host 340 performs a review and a determination based on captured image of defect, the reexamination host 320 carries out them based on real-time an image taken by the camera of the test device 310 in real time.

The alarm host 370 serves to monitor the state of the test device 310 and call an operator when a mode is changed to other one.

Figure 4:
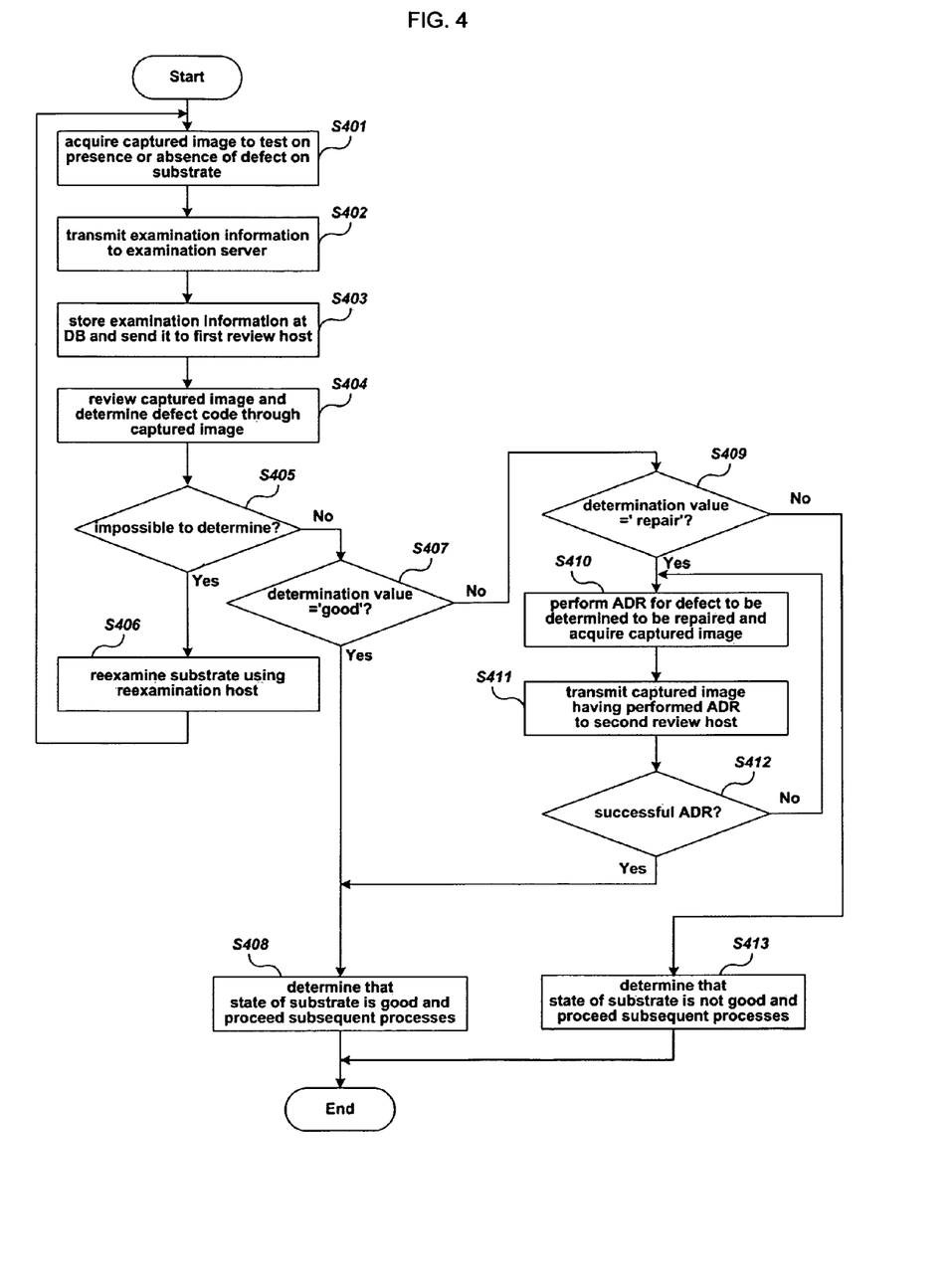
FIG. 4 is a flow chart of illustrating another operation of a test method using a virtual review according to the second embodiment of the present invention.

FIG. 4 is a flow chart of illustrating an operation of a test method using a virtual review according to the second embodiment of the present invention.

First, if a glass substrate is loaded, then it is determined by the test device 310 whether a defect exists on the array substrate or the color filter substrate. If any defect is detected on the array substrate or color filter substrate, then the test device 310 captures an image of the detected defect (S401).

Then, the test device 310 sends defect information including a GLS ID, a PNL ID, a defect serial number, etc. and information including a defect image file and the device number for each of the detected defect to the main server 330 (S402).

Next, the main server 330 stores the defect information and the information such as the captured image file, device number, etc. transmitted from the test device 310 at the database, and then sends them sequentially to the first review host 340 (S403).

If the defect information and the information such as the captured image file, device number, etc. are transmitted from the main server 330 to the first review host 340, then the review host 340 performs a review and a determination of a defect code based on the captured image file of defect (S404). That is, an operator opens the captured image file of the defect to review the defect and determine the state of the defect, and the determination value is transmitted to the main server 330.

Next, it is determined in step S405 whether it is possible or not to evaluate the defect on the array substrate or color filter. At this time, in the case where any one of "Q", "A", and "M", which mean it is difficult to determine the state of defect, is yielded as a determination value, the reexamination host 320 performs a reexamination of the defect (S406).

At this time, while the first review host 340 performs a review and a determination based on captured image of defect, the reexamination host 320 carries out, in real time, the review and determination based on a real-time image of the array substrate or color filter substrate taken by the camera of the test device 310.

On the other hand, in the case where it is possible to determine whether there is a defect on the array substrate and color filter substrate, it is determined in the step S407 whether the determination value is "G", which means 'good'. If the determination value is "G", then the array substrate and color filter substrate are determined to be good and subsequent processes are carried out (S408).

Unless the determination value is determined to be 'good', then it is determined whether the determination value is "P", which means to be repaired (S409).

If the determination value is "P", then the main server 330 sends information related to the defect and information that the determination value is "P" to the test device 310.

If the test device 310 receives the information that the determination value is "P" from the main server 330, then the test device 310 repairs the corresponding defect automatically and captures an image of the repaired region (S410).

At this time, the captured image of the repaired region is transmitted to the main server 330. Subsequently, the main server 330 stores the captured image of repaired region transmitted from the test device 310 at the database and then resends them to the second review host 360 (S4110).

Next, the second review host 360 determines whether the defect was repaired successfully, i.e. whether ADR (Auto defect repair) was successful or not, using the captured image of the repaired region transmitted from the server 330 (S412).

Then, if the result of the ADR showed that the defect was successfully repaired, more specifically, the defect was successfully repaired and it was determined that a defect does not exist on the array substrate or color filter substrate, the above mentioned step S408 continues and subsequently the next array substrate or color filter substrate may undergo the test to determine whether a defect exists or not.

In the case where the defect still exists in spite of the defect having been repaired, i.e., the ADR is not determined to be successful, then the test device 310 returns this process to the step of repairing the defect S410.

If the determination value is not "P", which means to be repaired, then the array substrate or color filter substrate is determined to have a defect and subsequent processes are performed (S413).

Here, the order of step S405, step S407, and step S409 can be changed.

Figure 5:
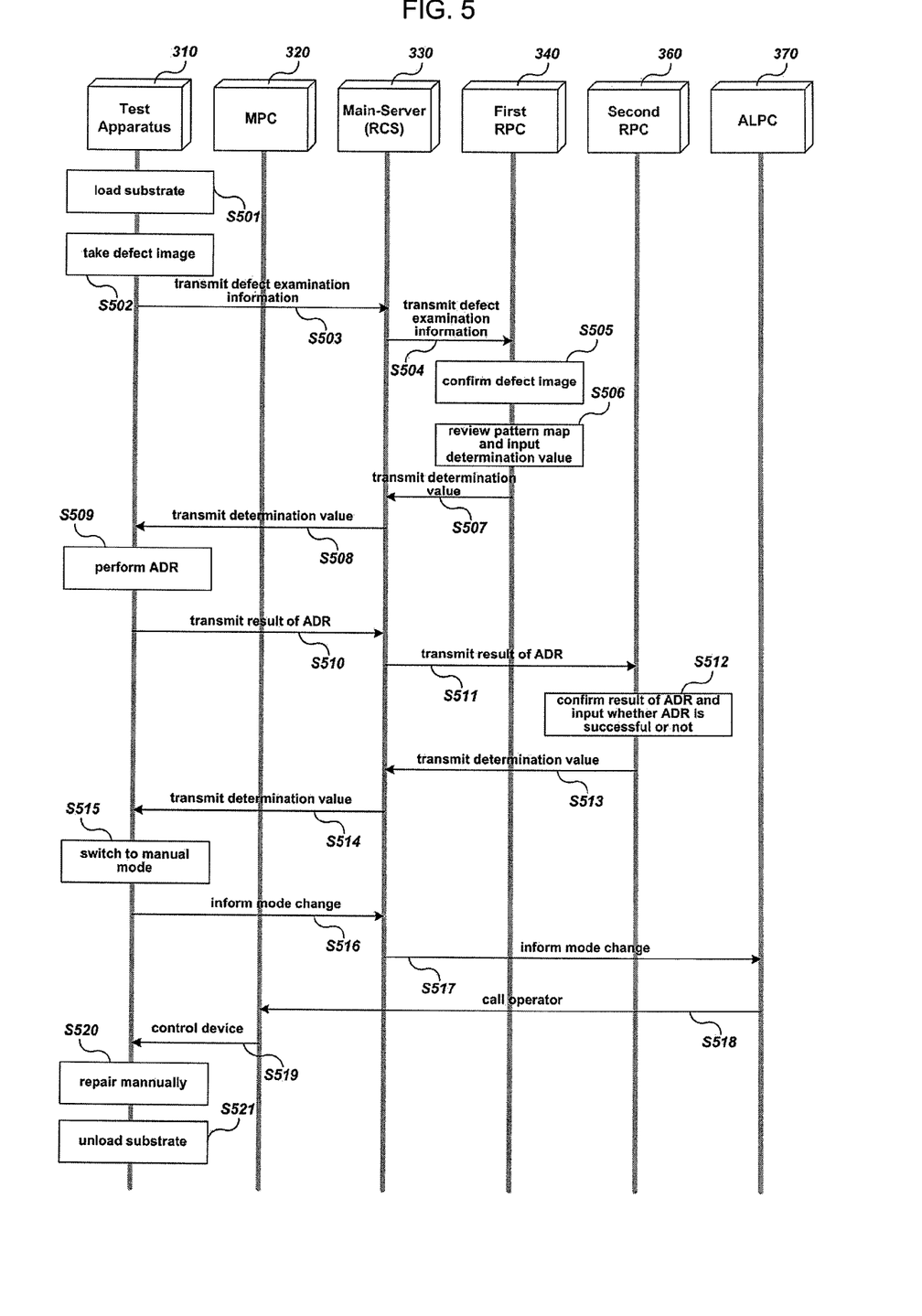
FIG. 5 is a signal flow diagram of the test system using the virtual review according to the second embodiment of the present invention.

FIG. 5 is a signal flow diagram of the test system using the virtual review according to the second embodiment of the present invention, and describes the operations of each component more specifically.

Referring to FIG. 5, in the test system using a virtual review according to the second embodiment of the present invention, the test device 310 first loads a glass substrate (S501), takes an image of the defect on the array substrate or color filter substrate (S502), and then sends the examination information of the defect to the main server 330 (S503).

The main server 330 resends the examination information to the first review host 340 adequately taking into account the amount of load (S504). At this time, the first review host 340 confirms the image of defect (S505), reviews a pattern map, and then inputs a determination value of the defect code (S506). Then, the determination value is transmitted to the main server 330 (S507).

Next, the main server 330 resends the determination value to the test device 310 (S508), and in the case where the determination value is "P" which means to be repaired, the test device 310 starts to perform ADR (S509). Then, the test device 310 sends the result of ADR to the main server 330 (S510).

The main server 330 resends the result of ADR to the second review host 360 adequately taking into account the amount of load (S511). Accordingly, the second review host 360 confirms the result of ADR, determines whether the ADR was successfully performed, and then inputs the determination value (S512).

Next, the second review host 360 sends the determination value on whether the ADR was successfully performed to the main server 330 (S513), and the main server 330 resends the determination value to the test device 310 (S514).

On the other hand, the test device 310 switches to a manual mode in the case where it is determined to be impossible for the main server 330 to determine whether there is a defect on the array substrate or color filter substrate (S515).

When switching to the manual mode, the test device 310 informs the main server 330 of the mode change (S516), and the main server 330 transfers the mode change to the alarm host 370 (S517).

Next, the alarm host 370 calls the operator of the reexamination host 320, which is a manually operated PC, corresponding to the mode change (S518). Accordingly, the operator manually repairs the defect on the array substrate or color filter substrate with the reexamination host 320 controlling the test device directly, which allows the test device 310 to manually repair the defect whose code is referred to as 'impossible to determine' (S520).

Subsequently, the substrate having the repaired defect is unloaded, then the next substrate is loaded, and then the steps S502 to S520 are repeated for the next substrate.

Figure 6A:
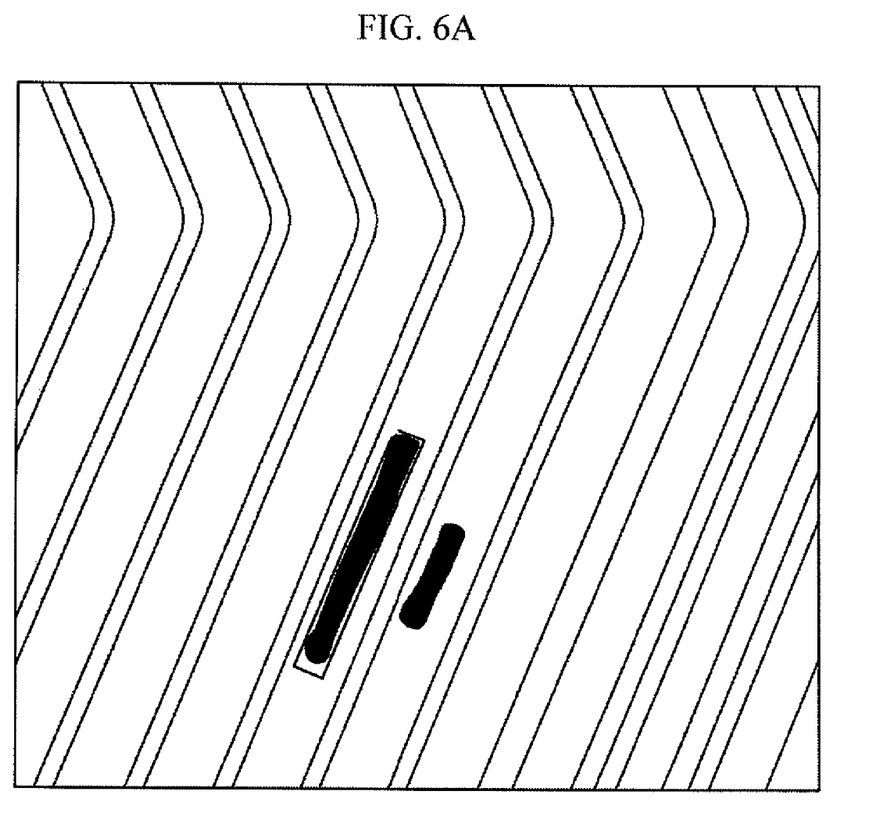
FIG. 6a is a photograph of captured image of illustrating a defect created according to the second embodiment of the present invention.
Figure 6B:
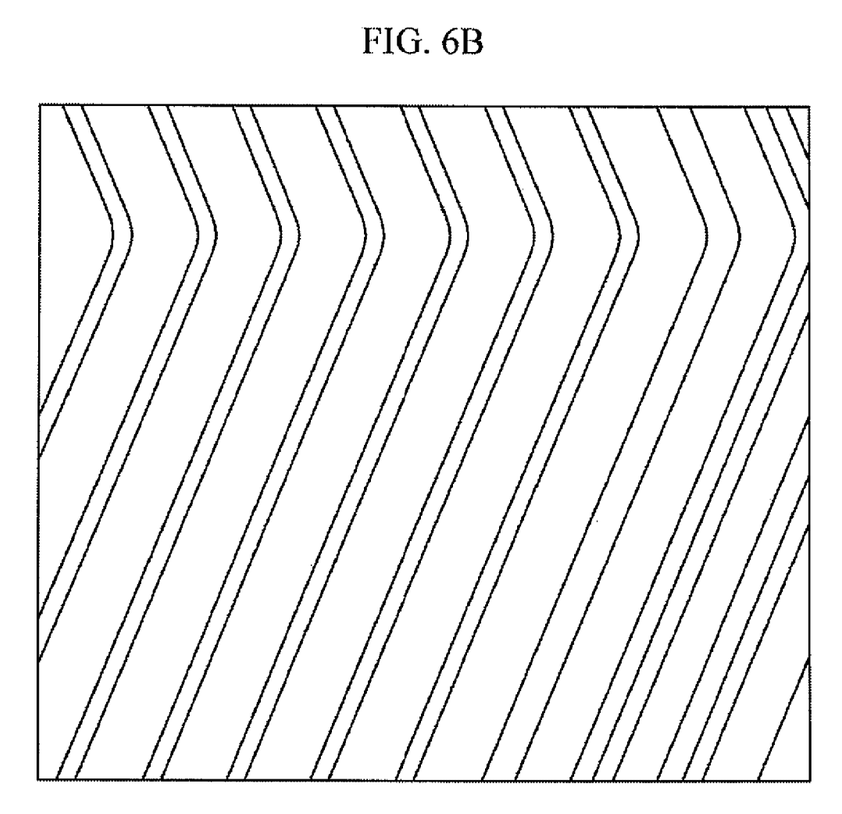
FIG. 6B is a photograph of captured image of illustrating a state after ADR.

FIG. 6A is a captured image illustrating a defect created according to the second embodiment of the present invention, and FIG. 6B is a captured image illustrating a state after ADR.

As can be seen in FIG. 6A, if the test device 310 captures an image of a defect, then the captured image is transmitted to the first review host 340 via the main server 330, and the first review host 340 reviews the captured image and determines its defect codes.

Subsequently, the test device 310 performs ADR and then sends the result of the ADR, i.e. the captured image, to the second review host 360 via the main server 330. FIG. 6B shows a state where the defect is eliminated from the captured image.

The foregoing embodiments and aspects of the invention are merely exemplary and are not to be construed as limiting the present invention. The present teaching can be readily applied to other types of apparatuses and methods. Also, the description of the exemplary embodiments of the present invention is intended to be illustrative, and not to limit the scope of the claims, and many alternatives, modifications, and variations will be apparent to those skilled in the art.

As mentioned above, the present invention allows one operator to perform review and determination based on image of defect on substrates captured by a plurality of test devices differently from the prior art in which one operator can control only one test device, thus allowing the test device to be driven efficiently and the number of operators to be reduced. As a consequence, work time for test can be substantially shortened.

What is claimed is:

1. A system for testing a defect of an array substrate or color filter substrate for use in a display device, comprising:
    a test device that takes an image of a defect on an array substrate or color filter substrate to acquire a captured image and provides the captured image and an information related to the defect;
    a main server that stores the captured image and the information related to the defect from the test device at a database and transmits the captured image and the information related to the defect; and
    a review host that receives the captured image and the information related to the defect and that determines whether the defect exists on the array substrate or the color filter substrate based on a status of the captured image from the main server to yield a determination result and send the determination result to the main server.

2. The system of claim 1, wherein the information related to the defect comprises,
    an ID of the array substrate or the color filter substrate, IDs of a plurality of panels provided on the array substrate or the color filter substrate, a defect serial number, an image file capturing the defect, and a serial number of the test device having detected the defect.

3. The system of claim 1, wherein the determination result comprises,
    a case where the defect is required to be repaired, a case where the state of defect is good, a case where the state of defect is not good, and a case where the state of defect is difficult to determine.

4. The system of claim 3, wherein if the determination result is the case where the defect is required to be repaired,
    a request for repair is made by the main server to the test device, and the defect is repaired by the test device.

5. The system of claim 4, wherein if the defect is repaired by the test device, a captured image of the repaired region is created and the captured image is transmitted from the test device to the main server.

6. The system of claim 1, further comprising:
    a quality management host that receives a captured image of a repaired area from the main server after the defect is repaired by the test device and determines whether a defect exists on the array substrate or color filter substrate based on the state of the captured image of the repaired area.

7. The system of claim 1, further comprising:
    an examination host that examines the state of the defect based on a real time image of the defect captured in real time in a case where the state of the captured image is difficult to determine.

8. A system for testing a defect of an array substrate or color filter substrate for use in a display device, comprising:

a test device that takes an image of a defect on an array substrate or color filter substrate to acquire a captured image and provides the captured image and an information related to the defect;

a main server that stores the captured image and the information related to the defect from the test device at a database and then transmits the captured image and the information related to the defect to a first review host, wherein the first review host determines whether a defect exists on the array substrate or color filter substrate based on a status of the captured image from the main server to yield a determination result and sends the determination result to the main server; and a second review host that receives a captured image of a repaired area from the main server and determines whether a defect exists on the array substrate or color filter substrate based on the state of the defect captured image of the repaired area.

9. The system of claim 8, wherein the information related to the defect comprises, an ID of the array substrate or color filter substrate, IDs of a plurality of panels provided on the array substrate or color filter substrate, a defect serial number, an image file capturing the defect, and a serial number of the test device having detected the defect.

10. The system of claim 8, wherein the determination result comprises, a case where the defect is required to be repaired, a case where the state of defect is good, a case where the state of defect is not good, and a case where the state of defect is difficult to determine.

11. The system of claim 10, wherein if the determination result is the case where the defect is required to be repaired, a request for repair is made by the main server to the test device, and the defect is repaired by the test device.

12. The system of claim 11, wherein if the defect is repaired by the test device, a captured image of the repaired region is created and the captured image is transmitted from the test device to the main server.

13. The system of claim 8, further comprising:

an examination host that examines the state of the defect based on a real time image of the defect captured in real time in a case where the state of the defect is difficult to determine.

14. The system of claim 8, further comprising:

an alarm host that monitors the state of the test device to thereby call an operator.

15. The system of claim 8, further comprising:

a sub-server that performs the same function as the main server in a case where the main server is not operated.

16. A method for testing a defect of an array substrate or color filter substrate for use in a display device, comprising:

taking an image of a defect on an array substrate or color filter substrate to acquire a captured image and providing the captured image and an information related to the defect from a test device;

storing the captured image and the information related to the defect from the test device at a database by a main server; and determining whether there is a defect on the array substrate or color filter substrate based on the captured image from the main server to yield a determination result and sending the determination result to the main server, wherein the determination result comprises a case where the defect is required to be repaired, a case where the state of defect is good, a case where the state of defect is not good and a case where the state of defect is difficult to determine.

17. The method of claim 16, wherein the information related to the defect comprises, an ID of the array substrate or color filter substrate, IDs of a plurality of panels provided on the array substrate or color filter substrate, a defect serial number, an image file capturing the defect, and a serial number of the test device having detected the defect.

18. The test method of claim 17, wherein if the determination result is the case where the defect is required to be repaired, a request for repair is made by the main server to the test device, and the defect is repaired by the test device.

19. The method of claim 18, wherein if the defect is repaired by the test device, a captured image of the repaired region is created and the captured image is transmitted from the test device to the main server.

20. The method of claim 16, further comprising:

receiving the captured image from the main server and determining whether a defect exists on the array substrate or color filter substrate based on the state of the captured image.

21. The method of claim 16, further comprising:

examining the state of the defect based on a real time image of the defect captured in real time in a case where the state of the defect is difficult to determine.

* * * * *